US00PP34770P2

(12) United States Plant Patent
NeSmith

(10) Patent No.: US PP34,770 P2
(45) Date of Patent: Nov. 29, 2022

(54) SOUTHERN HIGHBUSH BLUEBERRY PLANT NAMED 'TH-1987'

(50) Latin Name: *Vaccinium corymbosum*
Varietal Denomination: TH-1987

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/746,376

(22) Filed: May 17, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Karen M Redden
(74) *Attorney, Agent, or Firm* — Thomas Horstemeyer, LLP

(57) ABSTRACT

A new and distinct cultivar of *Vaccinium* plant named 'TH-1987', characterized by a combination of early season ripening and flowering, large berries with good flavor, firmness, and scar; and a low chill requirement about 150 hours, or less, below about 45° F.

5 Drawing Sheets

Botanical designation: *Vaccinium corymbosum.*
Cultivar denomination: 'TH-1987'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-1987'.

The new *Vaccinium corymbosum* 'TH-1987' was first identified by the inventor in 2013 in Griffin, Ga. The new variety 'TH-1987' exhibits early season ripening and flowering. 'TH-1987' also produces large berries with good flavor, firmness, and scar compared to representative cultivars. It also has a low chill requirement of about 150 hours, or less, below about 45° F. when produced under typical low to mid chill production areas in temperate regions.

'TH-1987' originated from seeds collected from open-pollinated fruit of *Vaccinium corymbosum* 'Snowchaser' (U.S. Plant Pat. No. 19,503). The open-pollenated fruit were harvested from selection trial plots in 2010 by D. Scott NeSmith. The new 'TH-1987' has been tested in asexually propagated (by vegetative cuttings) plantings a research farm in Alapaha, Ga. since 2014 where it was established for testing and comparing to industry standards. In 2017, the variety was entered into preliminary trials with a cooperator in Mexico. Observations of the resulting 'TH-1987' progeny have shown that the unique features of this new *Vaccinium corymbosum* 'TH-1987' are stable and reproduced true to type in successive generations

SUMMARY OF THE INVENTION

The new *Vaccinium* cultivar 'TH-1987 has not been observed under all possible environmental conditions. The phenotype may vary somewhat with variations in environment and cultural practices such as temperature, water and fertility levels, soil types, and light intensity without, however, any variance in genotype.

'TH-1987' is being released for commercial usage. The following traits have been repeatedly observed and are determined to be the unique and distinguishing characteristics of the new *Vaccinium corymbosum* cultivar named 'TH-896'. In combination, these traits set 'TH-896' apart from all other existing varieties of southern highbush blueberry known to the inventors:

1. early season and begins ripening after the early variety Georgia Dawn® ('TH-819' U.S. Plant Pat. No. 24,696) in south Georgia, but before 'Rebel' (U.S. Plant Pat. No. 18,138);
2. has berries that are larger than Georgia Dawn® at Alapaha (Table 1) and larger than its maternal parent 'Snowchaser';
3. produces berries that have a more aromatic flavor and better sweet/acid flavor balance as compared to 'Rebel' (Table 1).
4. low chilling requirement of about 150 hours, or less, below about 45° F. (based on comparison of flowering dates with those of known standard cultivars).

No notable diseases or other pest problems have been observed for the new variety that are not also common for other varieties. The male parent is unknown, and as compared to maternal parent 'Snowchaser', the new 'TH-1987' has a lower chill requirement, of about 150 hours, or less, below about 45° F., when produced under typical low to mid chill production areas in temperate regions. Due to the very low chill requirement, 'TH-1987' flowers very early and requires frost protection for successful production in temperate regions.

Preliminary trials of 'TH-1987' in "no-chill" regions of lower latitude in Mexico have indicated it performs well as an evergreen or ever bearing variety. Finding varieties that produce well in such regions is a challenge, and observations have revealed that 'TH-1987' appears to have the potential to adapt to such conditions. Comparisons to commercial varieties Georgia Dawn® and 'Rebel' are provided in Table 1, below.

TABLE 1

Plant and fruit ratings for 'TH-1987' and standards at Alapaha, Ga. Data represents a 3-Year avg (2016, 2020 and 2021). Rating scales are based on a 1 to 10 score, with 1 being the least desirable and 10 being the most desirable. Plants evaluated in 2016 were established in 2014, and those evaluated in 2020 and 2021 were established in 2018.

| | Georgia Dawn ® | 'Rebel' | 'TH-1987' |
|---|---|---|---|
| Berry size | 6.9 | 7.5 | 7.3 |
| Berry scar | 7.0 | 7.2 | 7.0 |
| Berry color | 7.0 | 7.2 | 7.0 |
| Berry firmness | 6.8 | 7.2 | 7.0 |
| Berry flavor | 7.2 | 6.0 | 7.0 |
| Cropping | 5.0 | 7.0 | 5.0 |
| Plant vigor | 8.0 | 7.8 | 7.8 |
| Date of 50% flowering | Feb. 9 | Feb. 15 | Feb. 1 |
| Date of 50% ripening | Apr. 20 | Apr. 25 | Apr. 24 |
| Fruit development period (days) | 69 | 69 | 82 |

BRIEF DESCRIPTION OF THE DRAWINGS

The accompanying colored photographic illustrations show the overall appearance and distinct characteristics of the new cultivar of *Vaccinium corymbosum* 'TH-1987' showing the colors as true as possible. Colors in the photographs may differ slightly from the color values cited in the detailed botanical description, which accurately describes the colors of the new *Vaccinium corymbosum* 'TH-1987'. Photographs were taken of plants grown outdoors in Alapaha, Ga. during different years.

The photograph labeled

The photograph labeled

The photograph labeled

The photograph labeled

The photographs labeled FIG. 5A is a close-up view of fruit of 'TH-1987' in a human hand, and FIG. 5B shows a cross sectional view of the interior of the fruit.

DETAILED BOTANICAL DESCRIPTION

Figure 1:
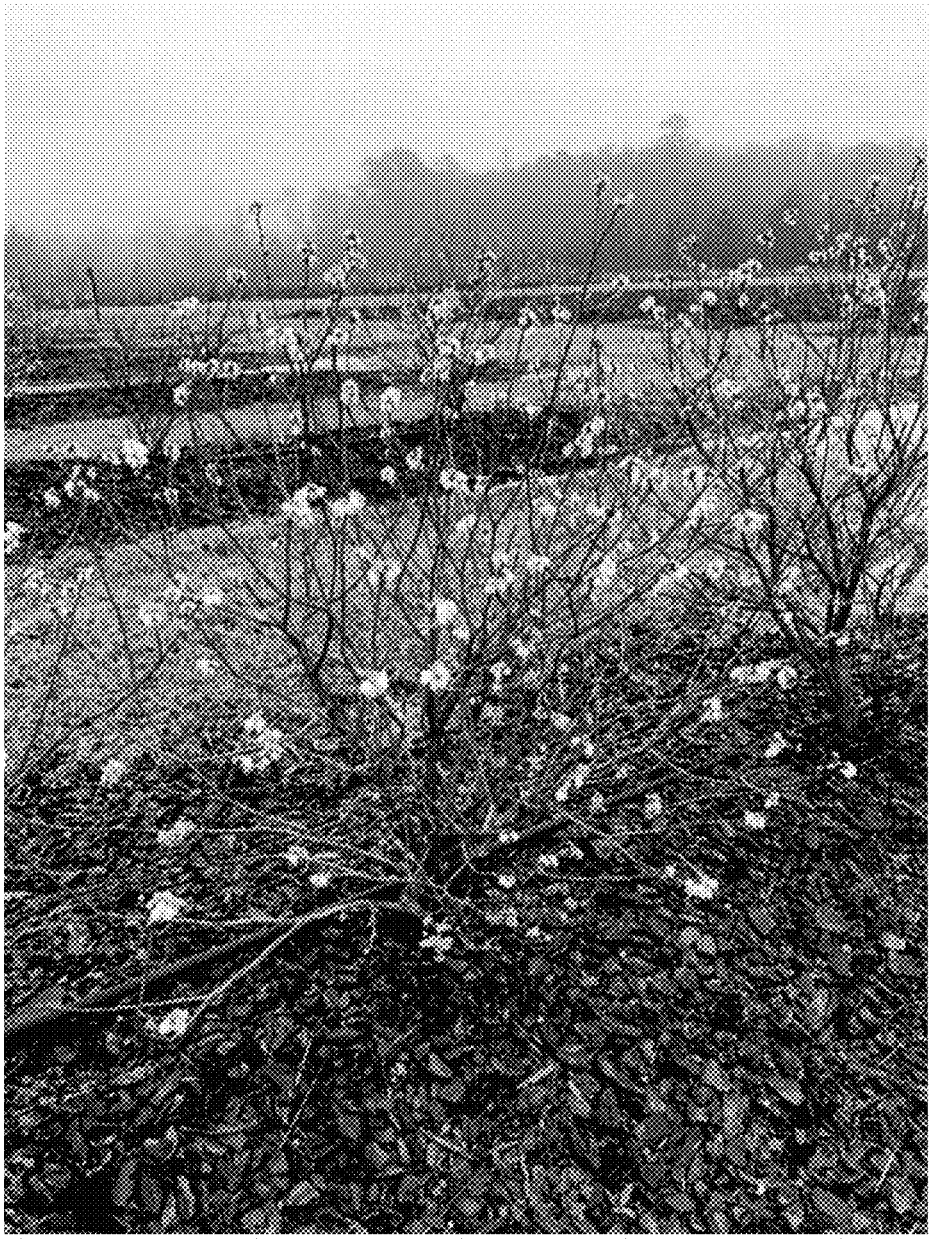
FIG. 1 depicts 'TH-1987' plants during flowering. Plants are 3 years old, and the photo was taken in February 2021 at Alapaha, Ga.
Figure 2:
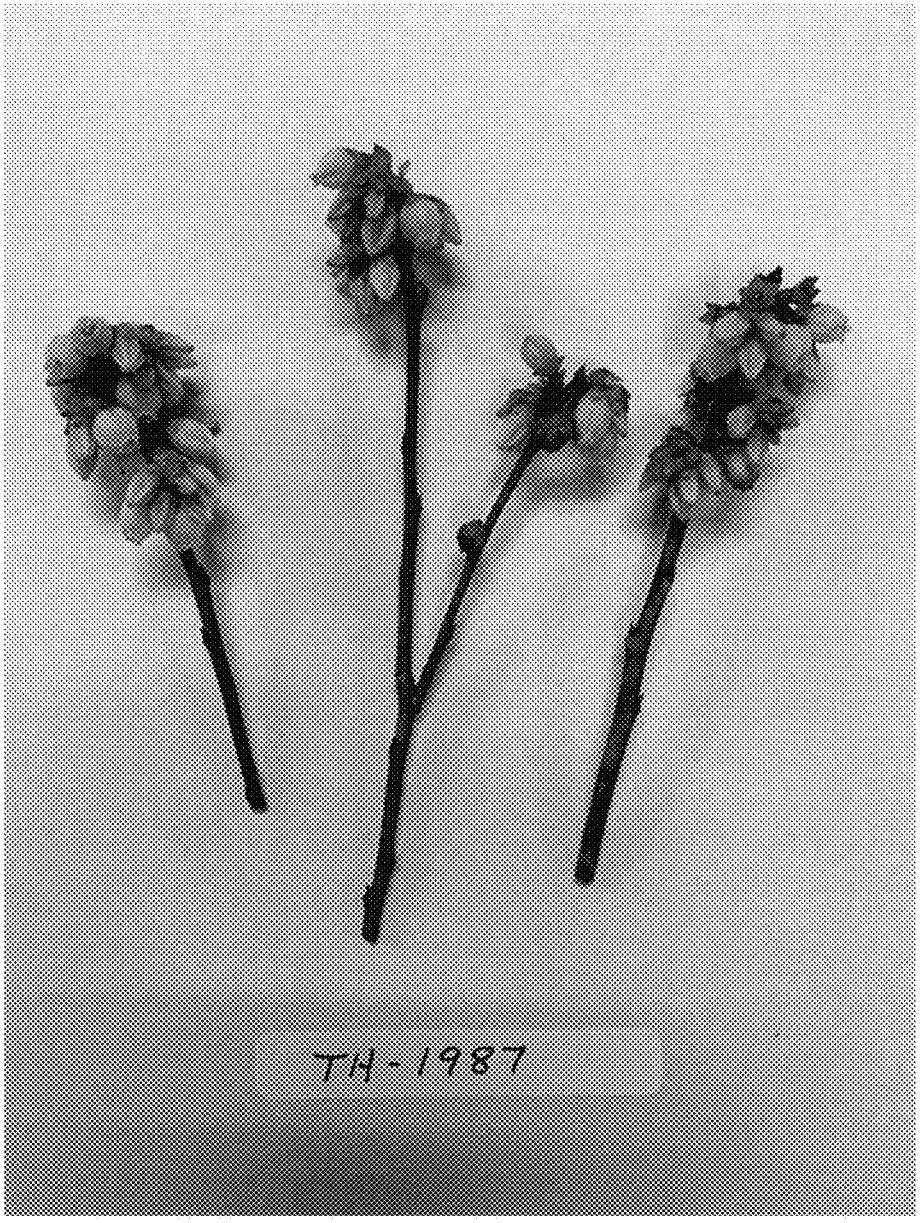
FIG. 2 depicts a close-up of 'TH-1987' flowers. Photo was taken in February 2021 at Alapaha, Ga.
Figure 3:
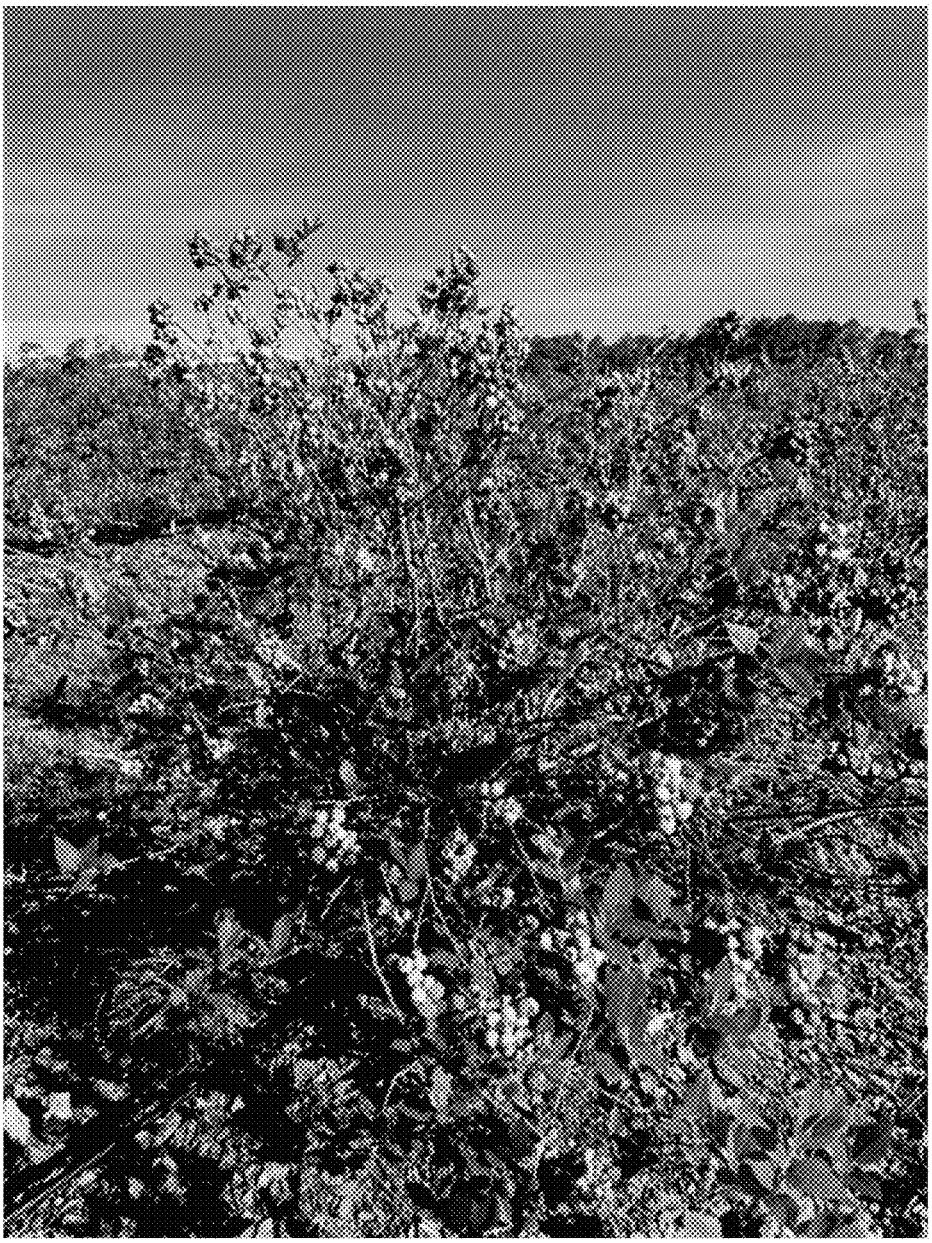
FIG. 3 depicts mature plants of 'TH-1987' during fruit ripening. Plants are 3 years old, and the photo was taken in April 2021 at Alapaha, Ga.
Figure 4:
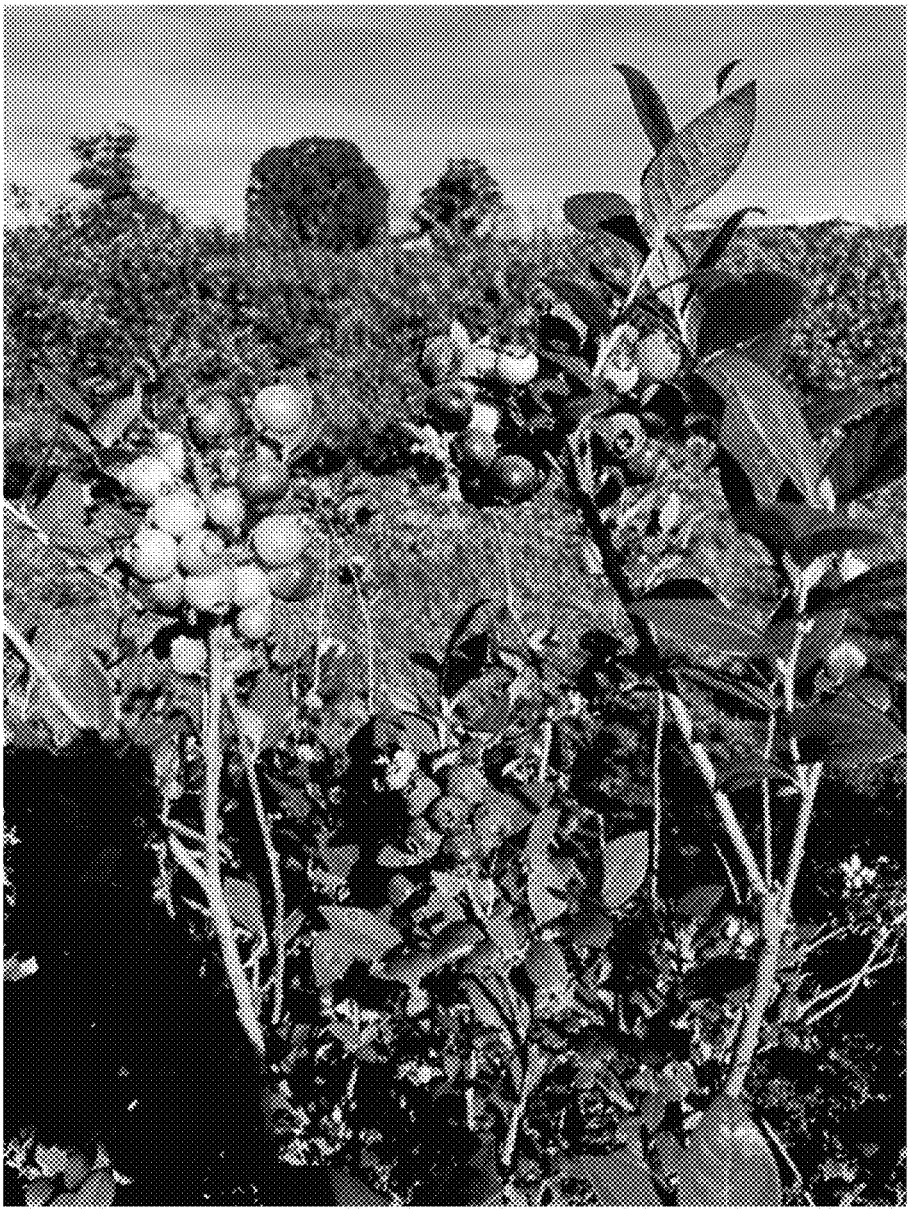
FIG. 4 depicts a close-up view of 'TH-1987' fruit on the plant. Plants are 3 years old, and the photo was taken in April 2021 at Alapaha, Ga.
Figure 5A:
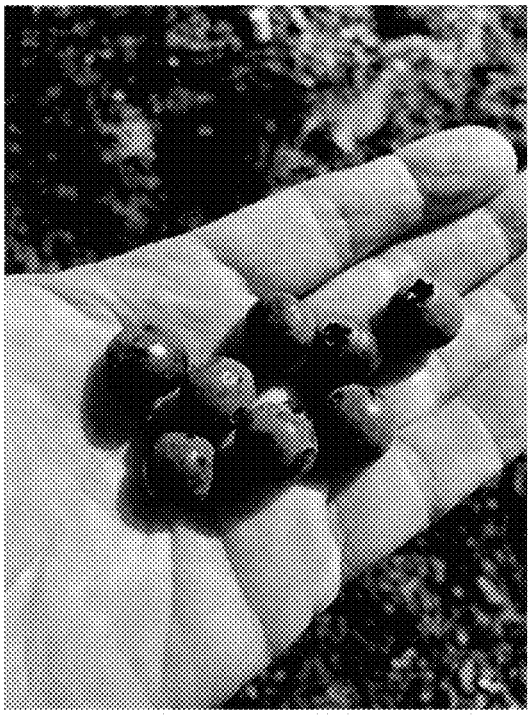
FIGS. 5A-5B depict close-up views of 'TH-1987' fruit.
Figure 5B:
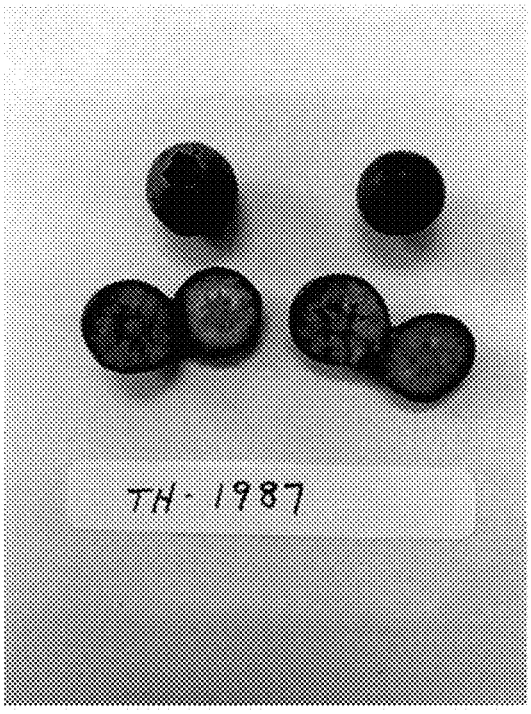

The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TH-1987'.

The following is a detailed description of the botanical and pomological characteristics of the subject blueberry clone. Where dimensions, sizes, colors, and other characteristics are given, it is to be understood that such characteristics are approximations and averages set forth as accurately as practicable. Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-1987'. Where dimensions, sizes, colors, and other characteristics are given, it is to be understood that such characteristics are approximations and averages set forth as accurately as practicable. Data were collected between the years of 2016-2021 from a farm in Alapaha, Ga. from 3 to 4-year-old plants (planted in the field with supplemental irrigation). In this region, the long-term average annual low temperature ranges from about 54° F. to 58° F., and the average annual high temperature for the year ranges from about 78° F. to 82° F.

Botanical classification: *Vaccinium corymbosum* 'TH-1987'.

*Commercial classification.*—Fruit-bearing shrub.

*Parentage.*—Originated from seeds collected from open-pollinated fruit of 'Snowchaser' (U.S. Plant Pat. No. 19,503).

Growth and propagation:

*Propagation type.*—Vegetative by softwood cuttings.

*Growth rate.*—Plant vigor is medium, canopy tends to stay compact.

*Root description.*—Fibrous.

Plant description:

*Size.*—About 1.2 to 1.4 m tall by about 4 years. The plant crown, or base, is narrow, typically about 10 to 20 cm in diameter. Upper portion of plant canopy reaches about 1.2 to 1.5 m in diameter by about 4 years.

*Usage.*—Primarily to be used as fresh fruit for shipping and processing markets.

*Growth habit.*—Plant is compact with a mostly spreading habit. Typically, there are 2 to 4 main canes arising from the crown, with multiple branching of shoots within 10 to 15 cm of the soil surface from those canes.

*Growth.*—Plants are moderately vigorous, dense canopy.

*Productivity.*—High crop/yield potential. Yields of about 7 to 10 lbs per plant are possible on plants about 4-years old or older grown under well fertilized and irrigated field conditions with frost protection.

*Cold hardiness.*—Similar to other early southern highbush varieties such as TH-819 Georgia Dawn® (U.S. Plant Pat. No. 24,696) and 'Rebel' (U.S. Plant Pat. No. 18,138).

*Disease resistance.*—No exceptional disease resistance or susceptibility observed. Typical for early season southern highbush such as Georgia Dawn® and 'Rebel'.

*Chilling requirement.*—Plants require 150 h or less, of temperatures at or below 7 C to induce normal leafing and flowering during the spring under conventional dormant production systems. 'TH-1987' has also shown a strong propensity for evergreen production with no chilling when grown under lower latitude locations such as Mexico.

*Leafing*.—Plants tend to break sufficient leaf buds simultaneously with, or shortly after, anthesis; however, heavy fruit set can suppress leaf development in some years.

*Canes*.—Main cane base diameter about 15 to 25 mm, color most near Grey 201B; two year old cane diameter about 10 to 15 mm, color transitioning from Yellow Green 145B to Greyed Orange 166B; current season wood diameter about 4 to 8 mm, color Yellow Green 145B.

*Fruiting wood*.—Moderate number of twigs about 10 to 15 cm in length, with internode lengths of about 15 to 25 mm common.

Foliage:

*Leaf color*.—Healthy mature leaves: top side of leaf color is Green 137A, under side of leaf color is Yellow Green 138B.

*Leaf arrangement*.—Alternate, simple.

*Leaf shape*.—Elliptic.

*Leaf margins*.—Nearly entire.

*Leaf venation*.—Pinnate with moderate to heavy netting.

*Leaf apices*.—Broadly acute.

*Leaf bases*.—Acute.

*Leaf dimensions*.—Length: about 35 to 50 mm; width: about 25 to 30 mm.

*Petioles*.—Small, about 2.5 to 3.0 mm long, about 1.5 to 2.0 mm wide; Color: Yellow Green 145C.

*Texture*.—Leaf margins nearly smooth. Leaf surface (upper and lower) glaucous.

Flowers:

*Date of* 50% *anthesis*.—3-year average February 1 in southeast Georgia.

*Flower shape*.—Urceolate.

*Flower bud number*.—High to very high, averaging about 4 to 8 buds per fruiting shoot.

*Flowers per cluster*.—About 5 to 8.

*Flower fragrance*.—None noticed.

*Corolla color*.—White NN155C once fully expanded (open); Red Purple 62C can be observed in early stages of corolla expansion, especially in cool springs.

*Corolla length*.—About 8.5 to 9.5 mm.

*Corolla width*.—About 6.5 to 7.5 mm.

*Corolla aperture width*.—About 3.0 to 3.5 mm.

*Flower peduncle*.—Length about 3.0 to 6.0 mm; Color: Green 138D; streaks of Greyed Purple 184C can be observed during cool springs.

*Flower pedicel*.—Length about 3.0 to 3.5 mm; Color: Green 138D.

*Calyx* (*with sepals*).—Diameter: about 6.5 to 7.5 mm; Color: sepals Green 138D; calyx center Green 138B.

*Stamen*.—Length: about 6.5 to 7.5 mm; number per flower: about 10; filament color: Green White 157C.

*Style*.—Length: about 8.0 to 9.0 mm; Color: Yellow Green 145B.

*Pistil*.—Length: about 9.5 to 10.5 mm; ovary color: Green 138D.

*Anther*.—Length: about 3.5 to 4.5 mm; number: about 10; Color: Greyed Orange 165B.

*Pollen*.—Abundance: medium; Color: Yellow White 158C.

*Compatibility*.—The cultivar has a moderate degree of self-compatibility.

Fruit:

*Date of* 50% *maturity*.—3-year average around April 24 in southeast Georgia.

*Fruit development period*.—About 82 days in southeast Georgia.

*Berry color*.—With wax Violet Blue 98D to 97B; with wax removed Black 203C.

*Berry flesh color*.—Green White 157D to White 155C.

*Berry surface wax abundance*.—Medium to high.

*Berry weight*.—1st harvest: about 2.3 to 2.6 g; 2nd harvest about 1.9 to 2.1 g.

*Berry size*.—Height from calyx to scar: about 14 to 16 mm; diameter: about 15 to 17 mm.

*Berry shape*.—Nearly spherical shape.

*Fruit stem scar*.—Small, dry, with occasional tearing upon harvest.

*Calyx*.—Depth shallow, about 1.0 to 2.0 mm; width medium, about 3.0 to 5.0 mm; sepals often visible, usually erect when present, about 1 mm or less.

*Berry firmness*.—Fair to good firmness.

*Berry flavor and texture*.—Texture smooth; only mildly sweet, low acidity.

*Storage quality*.—Fair to good.

*Suitability for mechanical harvesting*.—Not suitable.

*Uses*.—Primarily to be used as fresh fruit for shipping and processing markets.

Seed:

*Seed abundance in fruit*.—High, with about 15 to 20 fully developed seeds per berry.

*Seed color*.—Greyed Orange 165C.

*Seed dry weight*.—About 40 to 45 mg per 100 seed.

*Seed size*.—About 1.0 to 2.0 mm long.

It is claimed:

1. A new and distinct cultivar of the *Vaccinium* plant named 'TH-1987' as illustrated and described herein.

* * * * *